(12) United States Patent
Sakamoto et al.

(10) Patent No.: US 8,233,039 B2
(45) Date of Patent: Jul. 31, 2012

(54) MICROSCOPE IMAGE PICKUP SYSTEM

(75) Inventors: Shinya Sakamoto, Yokohama (JP);
Shinichiro Aizaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 909 days.

(21) Appl. No.: 12/327,033

(22) Filed: Dec. 3, 2008

(65) Prior Publication Data

US 2009/0102918 A1    Apr. 23, 2009

(30) Foreign Application Priority Data

Jun. 6, 2007    (JP) ................................ 2007-150406

(51) Int. Cl.
*H04N 7/18* (2006.01)
(52) U.S. Cl. ............ 348/79; 348/96; 348/495; 348/550; 382/254; 382/274; 382/299; 382/145; 382/284; 359/363; 359/388; 359/374; 359/368
(58) Field of Classification Search .................... 709/79, 709/370, 371, 362, 345; 348/79, 370, 371 348/362, 345
See application file for complete search history.

(56) References Cited

U.S. PATENT DOCUMENTS

| | | | |
|---|---|---|---|
| 7,492,958 B2 * | 2/2009 | Salmelin et al. | 382/255 |
| 7,706,624 B2 * | 4/2010 | Beazley | 382/260 |
| 2002/0030823 A1 * | 3/2002 | Kobayashi et al. | 356/485 |
| 2004/0095505 A1 * | 5/2004 | Gotanda | 348/370 |
| 2005/0248839 A1 | 11/2005 | Yamaguchi | |
| 2006/0171023 A1 | 8/2006 | Kishida | |
| 2006/0204236 A1 | 9/2006 | Sasaki et al. | |

FOREIGN PATENT DOCUMENTS

| | | |
|---|---|---|
| EP | 1 593 996 A2 | 11/2005 |
| JP | 2003-005084 A | 1/2003 |
| JP | 2003-029151 A | 1/2003 |
| JP | 2005-316036 A | 11/2005 |
| WO | WO 2008/028745 A1 | 3/2008 |

OTHER PUBLICATIONS

European Office Action dated Oct. 28, 2010 (in English) in counterpart European Application No. 08021188.1.
Extended European Search Report dated May 4, 2009 (5 pages), issued in counterpart European Application Serial No. 08021188.1.
Japanese Office Action dated Dec. 20, 2011 (and English translation thereof) in counterpart Japanese Application No. 2007-150406.

* cited by examiner

*Primary Examiner* — Jude Jean Gilles
(74) *Attorney, Agent, or Firm* — Holtz, Holtz, Goodman & Chick, PC

(57) ABSTRACT

A microscope image pickup system includes: alight source; an object lens; a display device; a record device; a capture device for performing a preview mode in which an image of the test object obtained by the object lens is repeatedly captured and a plurality of captured images are continuously displayed on the display device, or an image record mode in which the image of the test object is captured and the captured image is recorded on the record device; an illumination light amount control device for controlling the amount of light of the illumination light; and a system control device for controlling an operation of the illumination light amount control device depending on the preview mode or the image record mode performed by the capture device.

19 Claims, 10 Drawing Sheets

| QUANTITY OF LIGHT | ND FILTER | | | GAIN VALUE |
|---|---|---|---|---|
| P | 105a | 105b | 105c | Gp |
| P<Pa | ○ | × | × | Gs/Na |
| Pa≦P<Pb | × | ○ | × | Gs/Nb |
| Pb≦P<Pc | × | × | ○ | Gs/Nc |
| Pc≦P<Pd | ○ | ○ | × | Gs/(Na∗Nb) |
| Pd≦P<Pe | ○ | × | ○ | Gs/(Na∗Nc) |
| Pe≦P<Pf | × | ○ | ○ | Gs/(Nb∗Nc) |
| Pf≦P | ○ | ○ | ○ | Gs/(Na∗Nb∗Nc) |

FIG. 5

| SETTING ITEM | | ND FILTER | | | GAIN VALUE |
| --- | --- | --- | --- | --- | --- |
| IMAGE QUALITY LEVEL | FADING SUPPRESSION LEVEL | 105a | 105b | 105c | Gp |
| LOW | HIGH | × | × | ○ | Gs/Nc |
| MEDIUM | MEDIUM | × | ○ | × | Gs/Nb |
| HIGH | LOW | ○ | × | × | Gs/Na |

F I G. 8 A

| SETTING ITEM | | ND FILTER | | | GAIN VALUE |
| --- | --- | --- | --- | --- | --- |
| IMAGE QUALITY LEVEL | FADING SUPPRESSION LEVEL | 105a | 105b | 105c | Gp |
| LOW | HIGH | × | ○ | × | Gs/Nb |
| MEDIUM | MEDIUM | ○ | × | × | Gs/Na |
| HIGH | LOW | × | × | × | Gs |

FIG. 8B

MICROSCOPE IMAGE PICKUP SYSTEM

BACKGROUND OF THE INVENTION

1. Field of the Invention

The present invention relates to a microscope image pickup system for use in a fluorescent observation.

2. Description of the Related Art

In the medical and biological fields, a fluorescent observation method is used when protein, a gene, etc. in a cell of a living body are observed by a microscope. A fluorescent observation is a method in which a cell of a living body having a fluorescence indicator is irradiated with illumination light (exciting light) having a wavelength of only a specific width so that light having a wavelength (fluorescence) longer than that of the exciting light emitted from the cell of the living body. In addition, there are various capturing methods for capturing and displaying the fluorescence emitted from a cell of a living body, and images such as still images, moving pictures, etc. captured by an electronic image pickup device are not recorded, but preview images of a sample are displayed in real time.

However, a cell of a living body has the property of being damaged by the irradiation of exciting light, and gradually does no emit fluorescence in the process of the fluorescent observation. The phenomenon is referred to as fading. Therefore, some countermeasures have been devised not to make the sample of the cell of a living body faded.

For example, there is a microscope image pickup system for open/close controlling a cutoff device for a light source of a microscope depending on the operation mode of the image pickup device (for example, refer to Japanese Published Patent Application No. 2005-316036). The microscope image pickup system constantly irradiates a sample with exciting light when a preview image is displayed, and cuts off the exciting light after acquiring a still image when the still image is to be acquired. Thus, a sample can be protected from being unnecessarily irradiated by the exciting light. As a result, the fading of the sample can be suppressed.

SUMMARY OF THE INVENTION

The microscope image pickup system according to the present invention includes: a light source for emitting illumination light irradiating a test object; an object lens mounted opposite the test object; a display device; a record device; a capture device for performing a preview mode in which an image of the test object obtained by the object lens is repeatedly captured and a plurality of captured images are continuously displayed on the display device, or an image record mode in which the image of the test object is captured and the captured image is recorded on the record device; an illumination light amount control device for controlling an amount of light of the illumination light; and a system control device for controlling an operation of the illumination light amount control device depending on the preview mode or the image record mode performed by the capture device.

The system control device can also be configured to control the operation of the capture device depending on the preview mode or the image record mode performed by the capture device.

In addition, the system control device can further be configured to control the operation of the capture device depending on the operation of the illumination light amount control device.

The microscope image pickup system can be configured to include a calculation device for calculating an amount of light of the illumination light in the preview mode, and the system control device controls the operation of the illumination light amount control device and the operation of the capture device depending on the amount of light calculated by the calculation device.

The microscope image pickup system can be configured to include an image quality adjustment device for adjusting the quality of the image at a plurality of stages, and the system control device controls the operation of the illumination light amount adjustment device and the operation of the capture device depending on the combination of the quality at one of a plurality of stages adjusted by the image quality adjustment device and the preview mode or the image record mode performed by the capture device.

The microscope image pickup system according to the present invention includes: a light source for emitting illumination light irradiating a test object; an object lens mounted opposite the test object; a capture device for capturing an image of the test object by the object lens; an illumination light amount control device for controlling the amount of light of the illumination light; and a system control device for controlling the operation of the capture device depending on the operation of the illumination light amount control device.

The operation of the illumination light amount control device can be adjusting the entire transmittance of one or more darkening filters provided between the test object and the light source or the intensity of the illumination light of the light source.

The operation of the capture device can be adjusting the amplification rate of the signal value indicating the image, exposure time, white balance, or black balance.

BRIEF DESCRIPTION OF THE DRAWINGS

FIG. 5 shows the operation condition of the filter selection unit provided for the microscope image pickup system according to the second embodiment;

FIG. 8A shows the operation condition of the preview image quality setting unit provided for the microscope image pickup system according to the third embodiment;

FIG. 8B shows the operation condition of the image record quality setting unit provided for the microscope image pickup system according to the third embodiment;

DESCRIPTION OF THE PREFERRED EMBODIMENTS

The embodiments of the present invention are described below with reference to the attached drawings.

Figure 1:
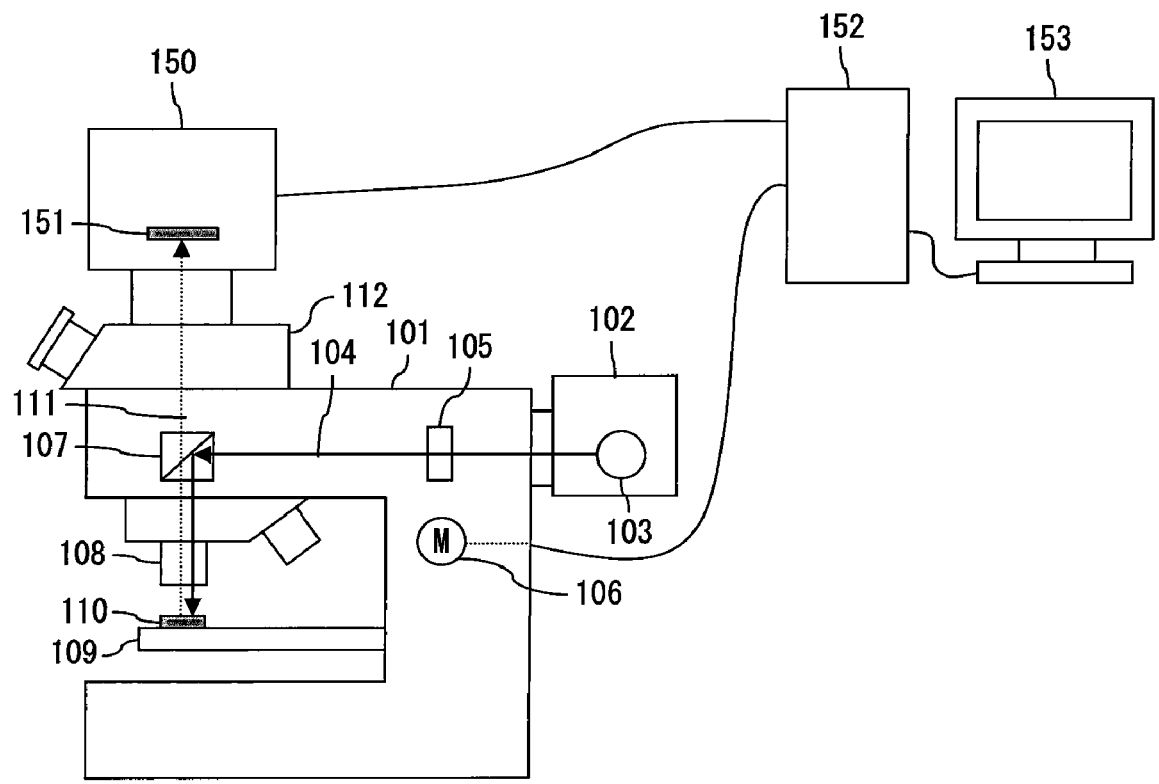
FIG. 1 shows the microscope image pickup system according to the first embodiment of the present invention.
Figure 2:
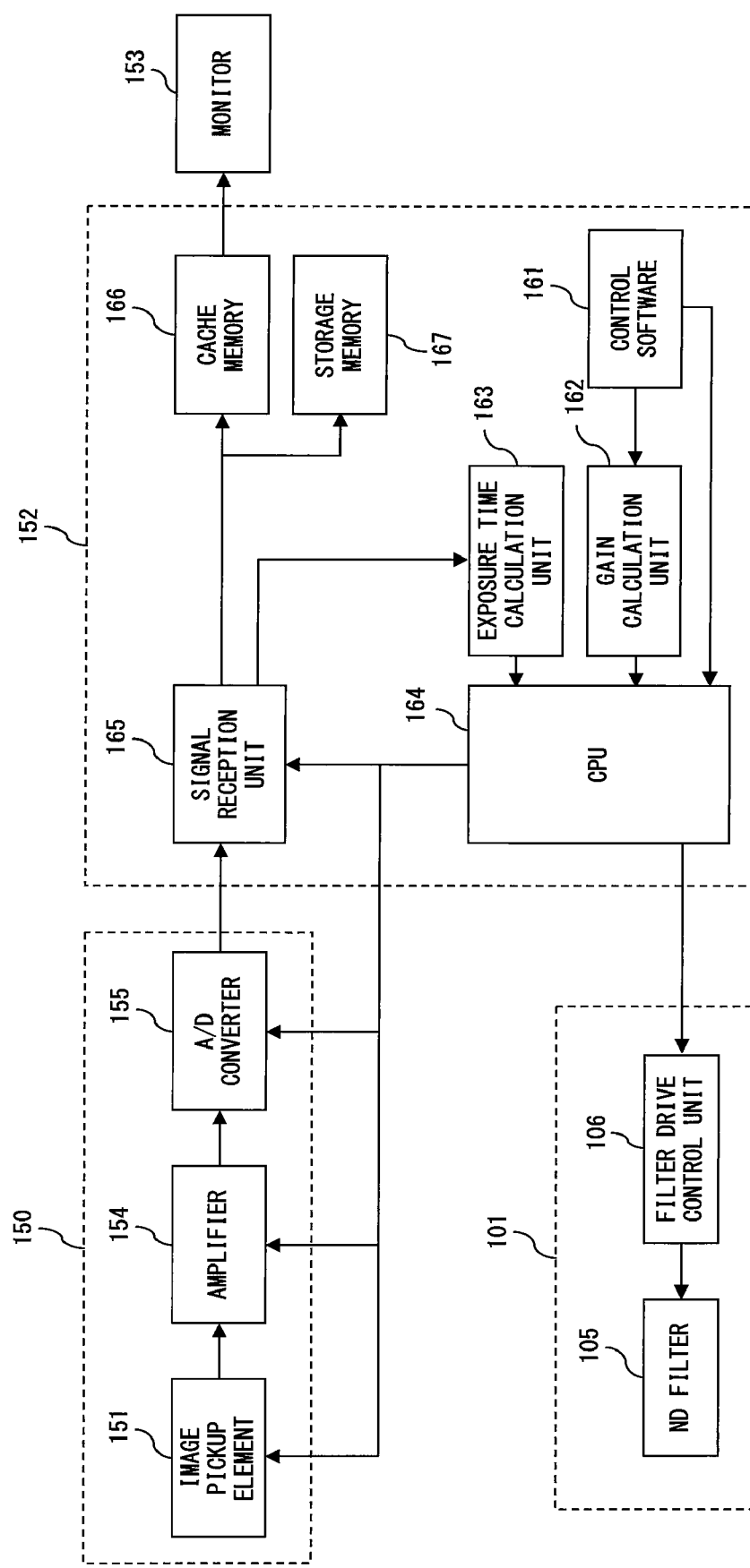
FIG. 2 shows the internal configuration of the microscope image pickup system according to the first embodiment.

FIG. 1 shows the microscope image pickup system according to the first embodiment of the present invention. FIG. 2 shows the internal configuration of the microscope image pickup system according to the first embodiment.

First, the configuration of the microscope image pickup system according to the first embodiment is described below with reference to FIGS. 1 and 2.

FIG. 1 or 2 shows a microscope 101, an illumination device 102 for emitting exciting light having only a specific wavelength, and a light source 103. Exciting light 104 emitted from the light source 103 in the illumination device 102 is irradiated into the inside of the microscope 101. FIGS. 1 and 2 also show a darkening filter 105 (hereinafter referred to as an ND filter), and a filter drive control unit 106. The ND filter 105 is drive controlled by the filter drive control unit 106, and is selectively inserted/removed on the optical path of the exciting light 104. FIG. 1 also shows a dichroic mirror 107. The dichroic mirror 107 is provided with a mirror for reflecting the exciting light 104 and transmitting the fluorescence 111 described later. The exciting light 104 is reflected by the dichroic mirror 107 and passes through an object lens 108, and then irradiates a sample 110 (test object) on a stage 109. The sample 110 receives the exciting light 104 and emits fluorescence 111 having a wavelength longer than that of the exciting light 104. The fluorescence 111 passes through the object lens 108, the dichroic mirror 107, and a barrel 112, and then introduced into an image pickup element 151 in an image pickup device 150.

FIGS. 1 and 2 also show a PC 152 and a monitor 153. The PC 152 and the image pickup device 150 are electrically connected to each other, and the PC 152 controls each unit of the image pickup device 150 by control software 161 through a CPU 164. Similarly, the PC 152 and the filter drive control unit 106 are electrically connected to each other, and the PC 152 controls the operation of the filter drive control unit 106 by the control software 161 through the CPU 164.

The image pickup device 150 is provided with the image pickup element 151, an amplifier 154, and an A/D converter 155. The amplifier 154 multiplies a signal value indicating an image transmitted from the image pickup element 151 by a predetermined gain value (amplification rate) for amplification. The control software 161 in the PC 152 controls the image pickup device 150, the filter drive control unit 106, and a gain calculation unit 162 by the operation input from an observer. The gain calculation unit 162 calculates the gain value of the amplifier 154 according to a signal from the control software 161. The exposure time calculation unit 163 calculates the exposure time of the image pickup element 151. The CPU 164 integrally controls each unit according to a signal from the control software 161. A signal reception unit 165 receives a signal value indicating an image transmitted from the image pickup device 150, and allocates the signal value indicating an image to cache memory 166 or storage memory 167 in a preview mode or an image record mode described later. The cache memory 166 has a memory area for storing a signal value indicating one image. The storage memory 167 has a memory area for storing plural still images and moving pictures.

Described below are the preview mode and the image record mode used in the microscope image pickup system according to the present embodiment. The preview mode or the image record mode is performed by the control software 161 by an observer issuing an instruction to the control software 161.

The preview mode is a function in which an image is fetched to the image pickup device 150 continuously in time, and is continuously displayed on the monitor 153. The order of the processes of a signal value indicating an image in the preview mode is described below. First, the signal value indicating an image obtained by the image pickup element 151 is amplified by the amplifier 154, converted into a digital value by the A/D converter 155, and transmitted to the signal reception unit 165. Next, the signal value indicating the image is transmitted from the signal reception unit 165 to the cache memory 166, and temporarily stored therein. A series of the processes are performed continuously in time, and the image stored in the cache memory 166 is updated at any time. The image obtained in the cache memory 166 is displayed continuously in time on the monitor 153.

The image record mode is a function in which a still image captured by the image pickup device 150 is stored. Described below is the order of the processes of the signal value indicating an image in the image record mode. First, the signal value indicating the image obtained by the image pickup element 151 is amplified by the amplifier 154, converted into a digital value by the A/D converter 155, and transmitted to the signal reception unit 165. Next, the signal value indicating the image is transmitted from the signal reception unit 165 to the storage memory 167, and stored therein. Although the image capturing operations are performed any number of times, the images recorded in the storage memory 167 are not updated, but the images are stored in different memory stores.

Figure 3:
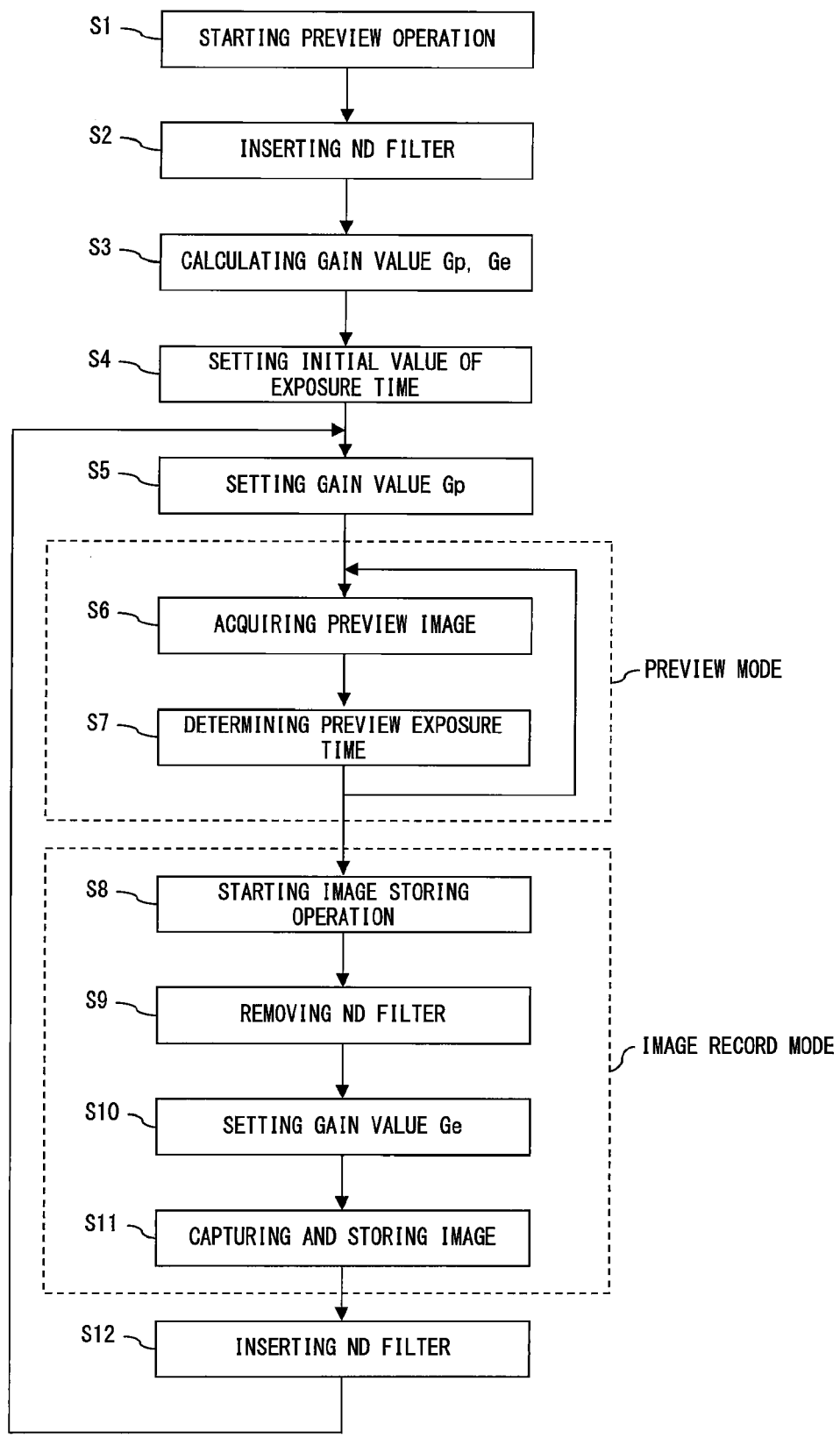
FIG. 3 is a flowchart for explanation of the operation of the microscope image pickup system according to the first embodiment.

FIG. 3 is a flowchart for explanation of the operation of the microscope image pickup system according to the first embodiment. The feature of the microscope image pickup system according to the first embodiment is to insert the ND filter 105 into the optical path of the exciting light 104 in the preview mode, and remove the ND filter 105 from the optical path of the exciting light 104 in the image record mode.

First, when an instruction to enter the preview mode is issued to the control software 161 by, for example, pressing a preview start button by an observer (S1), the control software 161 transmits a drive signal to the filter drive control unit 106 through the CPU 164, and inserts the ND filter 105 into the optical path of the exciting light 104 (S2).

Next, the control software 161 directs the gain calculation unit 162 to calculate the gain value Gp in the preview mode and the gain value Ge in the image record mode (S3). Assume that the transmittance of the ND filter 105 is N, and the gain of the amplifier 154 defined by an observer by the control software 161 is Gs, the gain value Gp in the preview mode is calculated by Gp=Gs/N, and the gain value Ge in the image record mode is Ge=Gs.

Next, the control software 161 transmits the initial value of a predetermined exposure time to a control unit for controlling the exposure time of the image pickup element 151 through the CPU 164, sets the exposure time of the image pickup element 151 (S4), transmits the gain value Gp calculated by the gain calculation unit 162 to the amplifier 154, and sets the gain value Gp (S5).

Then, the control software 161 transmits a capture start instruction again to the image pickup device 150 through the CPU 164, and acquires an image (S6).

Next, the control software 161 determines the exposure time in the preview mode (S7). The exposure time determined at this time is determined by an observer using the control software 161 or calculated by the exposure time calculation unit 163 using the image transmitted from the signal reception unit 165.

Next, the control software 161 transmits a capture start instruction to the image pickup device 150 through the CPU 164, and acquires an image (S6). In the preview mode, the processes in S6 and S7 are repeated. After the first process in S7, the image record mode can be used.

When the observer issues an instruction to enter the image record mode to the control software 161 by, for example, pressing an image storage button (S8), the control software 161 transmits a drive signal to the filter drive control unit 106 through the CPU 164, and removes the ND filter 105 from the optical path of the exciting light 104 (S9).

Next, the control software 161 transmits the exposure time determined in the preview mode in S7 to the control unit for controlling the exposure time of the image pickup element 151 through the CPU 164 to set the exposure time of the image pickup element 151, and transmits the gain value Ge calculated by the gain calculation unit 162 to the amplifier 154 to set the gain value Ge (S10).

Then, the control software 161 transmits a capture start instruction to the image pickup device 150 through the CPU 164, acquires an image, and records the image in the storage memory 167 (S11).

After a capturing operation is completed, the control software 161 transmits a drive signal again to the filter drive control unit 106 through the CPU 164, directs the ND filter 105 to enter the optical path of the exciting light 104 (S12), and returns control to the preview mode (S6, S7).

In the microscope image pickup system according to the first embodiment, the ND filter 105 enters the optical path of the exciting light 104 in the preview mode, and the intensity of the exciting light 104 irradiated onto the sample 110 can be reduced. Thus, the fading of the sample 110 in the preview mode can be suppressed.

According to the microscope image pickup system of the first embodiment, when the ND filter 105 is inserted in the preview mode, the gain value Gp of the amplifier 154 is set higher than the gain value Gs depending on the transmittance N of the ND filter 105. Therefore, the intensity of the fluorescence 111 of the sample 110 in the preview mode is equal to the intensity of the fluorescence 111 of the sample 110 originally observed when the ND filter 105 is removed, thereby guaranteeing the convenience during observation. In addition, since the gain value Ge of the amplifier 154 is equal to the gain value Gs when the ND filter 105 is removed in the image record mode, the image can be recorded in the storage memory 167 with the intensity of the fluorescence 111 of the originally observed sample 110, thereby storing a clear observed image in the image record mode.

Described next is the microscope image pickup system according to the second embodiment.

Figure 4:
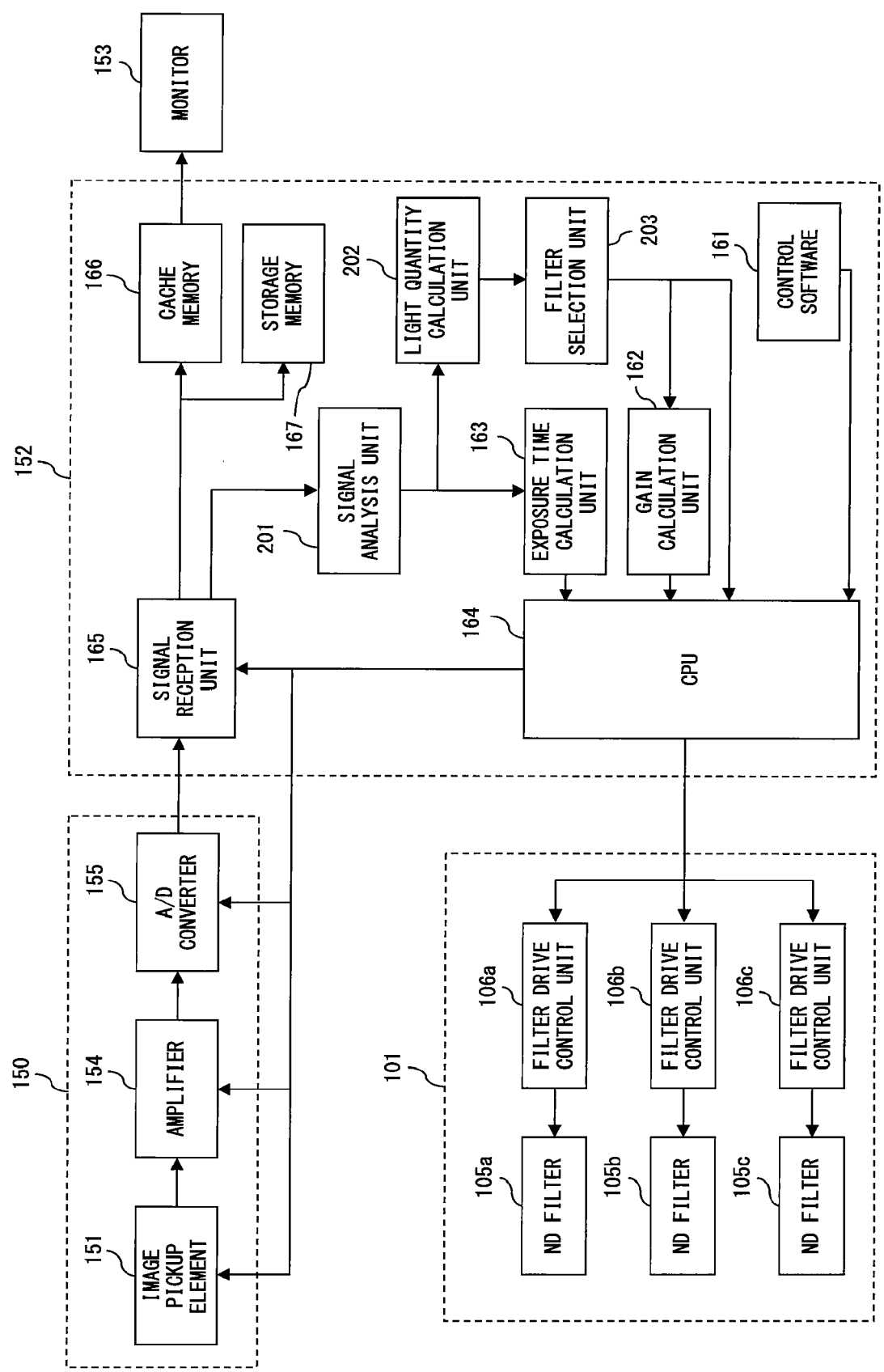
FIG. 4 shows the internal configuration of the microscope image pickup system according to the second embodiment.
Figure 6:
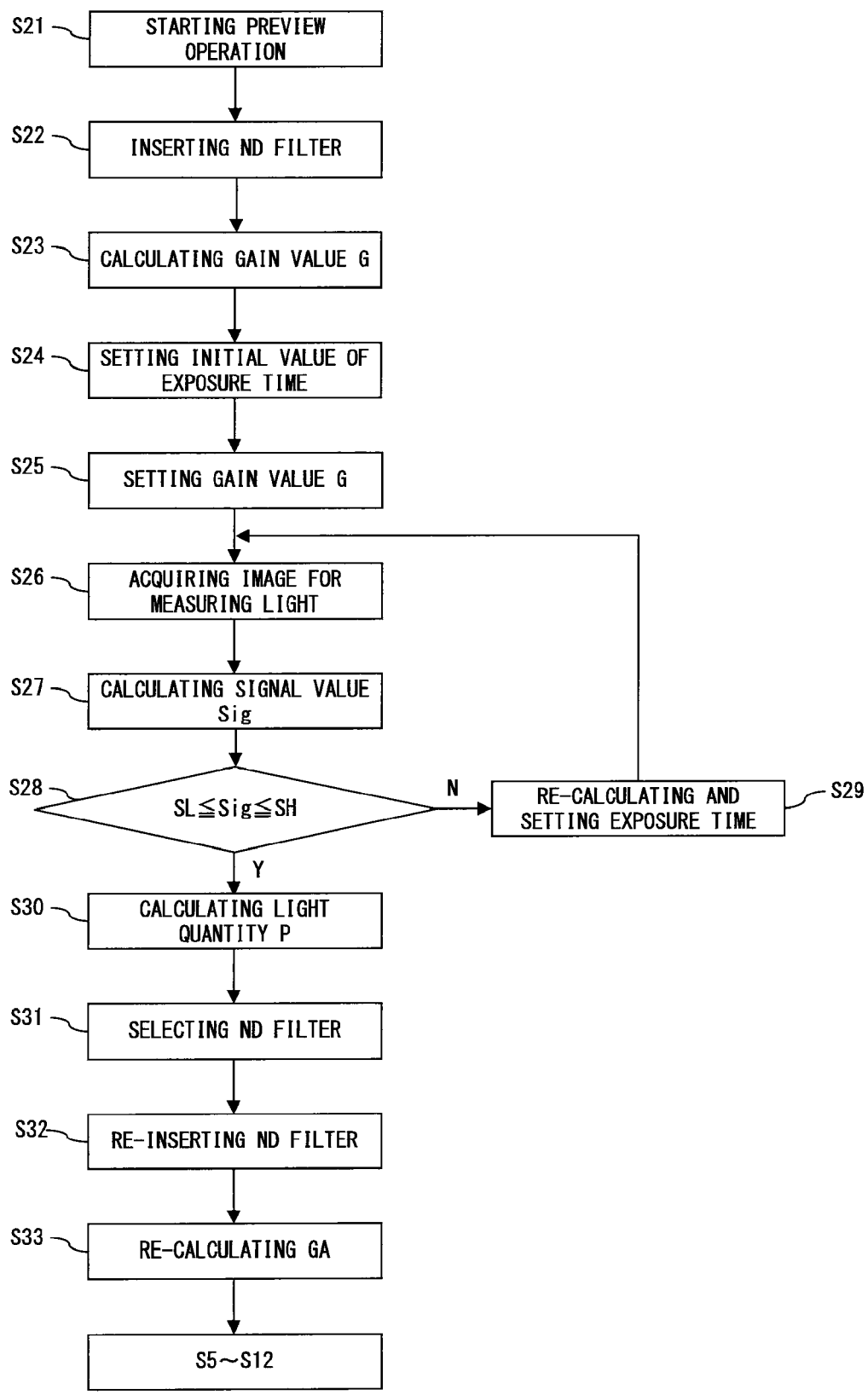
FIG. 6 is a flowchart for explanation of the operation of the microscope image pickup system according to the second embodiment.

FIG. 4 shows the internal configuration of the microscope image pickup system according to the second embodiment. FIG. 5 shows the operation condition of the filter selection unit provided for the microscope image pickup system according to the second embodiment. FIG. 6 is a flowchart for explanation of the operation of the microscope image pickup system according to the second embodiment. In FIG. 4, the same configuration as in the first embodiment is assigned the same reference numeral, and the description is omitted here.

As shown in FIG. 4, the microscope image pickup system according to the second embodiment is provided with ND filters 105a through 105c and filter drive control units 106a through 106c in the microscope 101. Additionally, the PC 152 is also provided with a signal analysis unit 201, a light quantity calculation unit 202, and a filter selection unit 203 in addition to the control software 161, the gain calculation unit 162, the exposure time calculation unit 163, the CPU 164, the signal reception unit 165, the cache memory 166, and the storage memory 167. In addition, the transmittance of the ND filter 105a is referred to as Na, the transmittance of the ND filter 105b is referred to as Nb, and the transmittance of the ND filter 105c is referred to as Nc (Na>Nb>Nc).

The filter drive control unit 106a controls the insert/remove drive of the ND filter 105a, the filter drive control unit 106b controls the insert/remove drive of the ND filter 105b, and the filter drive control unit 106c controls the insert/remove drive of the ND filter 105c.

The signal analysis unit 201 calculates the signal value Sig as the highest intensity from the signal value indicating an image received by the signal reception unit 165 in the preview mode. If the expression $SL \leqq Sig \leqq SH$ holds where SL and SH respectively indicate predetermined lower limit value SL and upper limit value SH, then the signal value Sig is transmitted to the light quantity calculation unit 202. If the expression Sig<SL or SH<Sig holds, the exposure time calculation unit 163 re-calculates the exposure time T and re-issues a capture start instruction to the image pickup device 150.

The light quantity calculation unit 202 calculates the light quantity P by the following Equation 1 using the gain value G calculated by the gain calculation unit 162, the exposure time T calculated by the exposure time calculation unit 163, the transmittance N of the ND filter 105 inserted during the measurement of light, and the signal value Sig calculated by the signal analysis unit 201. The calculated light quantity P is transmitted to the filter selection unit 203.

$$P = Sig/GTN \qquad \text{(Equation 1)}$$

The filter selection unit 203 selects the specific ND filter 105 from among the ND filters 105a through 105c depending on the light quantity P calculated by the light quantity calculation unit 202. That is, the filter selection unit 203 determines the ND filter 105 to be inserted onto the optical path of the exciting light 104 in the preview mode depending on the level of the quantity light P. The method of selecting the ND filter 105 is used by dividing the light quantity P by the thresholds Pa, Pb, Pc, Pd, Pe, Pf (Pa<Pb<Pc<Pd<Pe<Pf) under the operation conditions shown in FIG. 5. For example, when the light quantity P satisfies $Pc \leqq P < Pd$, the ND filter 105a and the ND filter 105b are selected.

In addition, the filter selection unit 203 transmits a signal indicating the selected ND filter 105 to the CPU 164, and the CPU 164 controls the operation of the filter drive control unit 106 corresponding to the ND filter 105 indicated by the signal. The filter selection unit 203 simultaneously transmits the signal indicating the selected ND filter 105 to the gain calculation unit 162. The gain calculation unit 162 calculates a gain value Gp on the basis of the entire transmittance N of the signal indicating the ND filter 105 transmitted from the filter selection unit 203. For example, when the signals indicating the ND filter 105a and the ND filter 105b are transmitted from the filter selection unit 203 to the gain calculation unit 162, the gain calculation unit 162 calculates the gain value Gp by the equation Gp=Gs/(Na*Nb) as shown in FIG. 5.

FIG. 6 is a flowchart for explanation of the operation of the microscope image pickup system according to the second embodiment.

First, when an observer issues an instruction to use the preview mode to the control software 161 by, for example, pressing the preview start button etc. (S21), the control software 161 transmits a drive signal to the filter drive control unit 106a through the CPU 164, and inserts the ND filter 105a onto the optical path of the exciting light 104 (S22).

Next, the control software 161 directs the gain calculation unit 162 to calculate the gain value G in the same method as in the first embodiment (S23). That is, the gain value G is obtained by G=Gs/Na.

The control software 161 transmits the initial value of a predetermined exposure time to a control unit for controlling the exposure time of the image pickup element 151 through the CPU 164 to set the exposure time of the image pickup element 151 (S24), and transmits the gain value G calculated by the gain calculation unit 162 to the amplifier 154 to set the gain value G (S25).

Next, the control software 161 transmits a capture start instruction to the image pickup device 150 through the CPU 164 and acquires a captured image for measurement of light (S26).

Then, the control software 161 directs the signal analysis unit 201 to calculate the signal value Sig using the image for the measurement of light obtained in S26 (S27). At this time, the signal analysis unit 201 determines whether or not the signal value Sig is a value within a predetermined range (SL≦Sig≦SH) (S28).

When the signal value Sig is out of the range (NO in S28), the control software 161 re-calculates the exposure time by automatically setting the exposure by feedback control of the exposure time calculation unit 163 to set the exposure time (S29) and re-acquire an image for measurement of light (S26).

On the other hand, when it is determined that the signal value Sig is within a predetermined range (YES in S28), the control software 161 directs the light quantity calculation unit 202 to calculate the light quantity P using the gain value G, the exposure time T, the transmittance N, and the signal value Sig (S30).

Next, the control software 161 directs the filter selection unit 203 to select the ND filter 105 corresponding to the light quantity P calculated by the light quantity calculation unit 202 under the operation condition shown in FIG. 5 (S31).

Next, the control software 161 inserts the ND filter 105 selected by the filter selection unit 203 in S31 (S32).

The control software 161 directs the gain calculation unit 162 to calculate the gain value Gp on the basis of the entire transmittance N of the ND filter 105 selected by the filter selection unit 203 (S33).

Afterwards, the operations in the preview mode and the image record mode similar to those in S5 through S12 according to the first embodiment are performed.

According to the microscope image pickup system of the second embodiment, the ND filter 105 is selectively inserted so that the intensity of the exciting light 104 irradiated on the sample 110 in the preview mode can be appropriate depending on the quantity light P entering the image pickup device 150. Thus, since the intensity of the exciting light 104 irradiated on the sample 110 can be appropriately adjusted although using the light source 103 emitting unnecessarily intense exciting light 104, the sample 110 can be appropriately protected against fading.

According to the microscope image pickup system of the second embodiment, since the operation conditions for the selection of the ND filter 105, the calculation of a gain value Gp, etc. are automatically adjusted without specific operations of an observer, the operability of the microscope 101 can be improved.

In addition, according to the microscope image pickup system of the second embodiment, as with the microscope image pickup system of the first embodiment, when the ND filter 105 is inserted in the preview mode, the gain value Gp of the amplifier 154 is set higher than the gain value Gs depending on the entire transmittance N of the ND filter 105. Therefore, the intensity of the fluorescence 111 of the sample 110 in the preview mode is equivalent to the intensity of the fluorescence 111 of the sample 110 to be originally observed when the ND filter 105 is removed, thereby successfully maintaining the convenience during observation. In addition, when the ND filter 105 is removed in the image record mode, the gain value Ge of the amplifier 154 is equal to the gain value Gs. Therefore, an image can be recorded in the storage memory 167 with the intensity of the fluorescence 111 of the sample 110 to be originally obtained, thereby storing a clear observed image in the image record mode.

Described next is the microscope image pickup system according to the third embodiment of the present invention.

Figure 7:
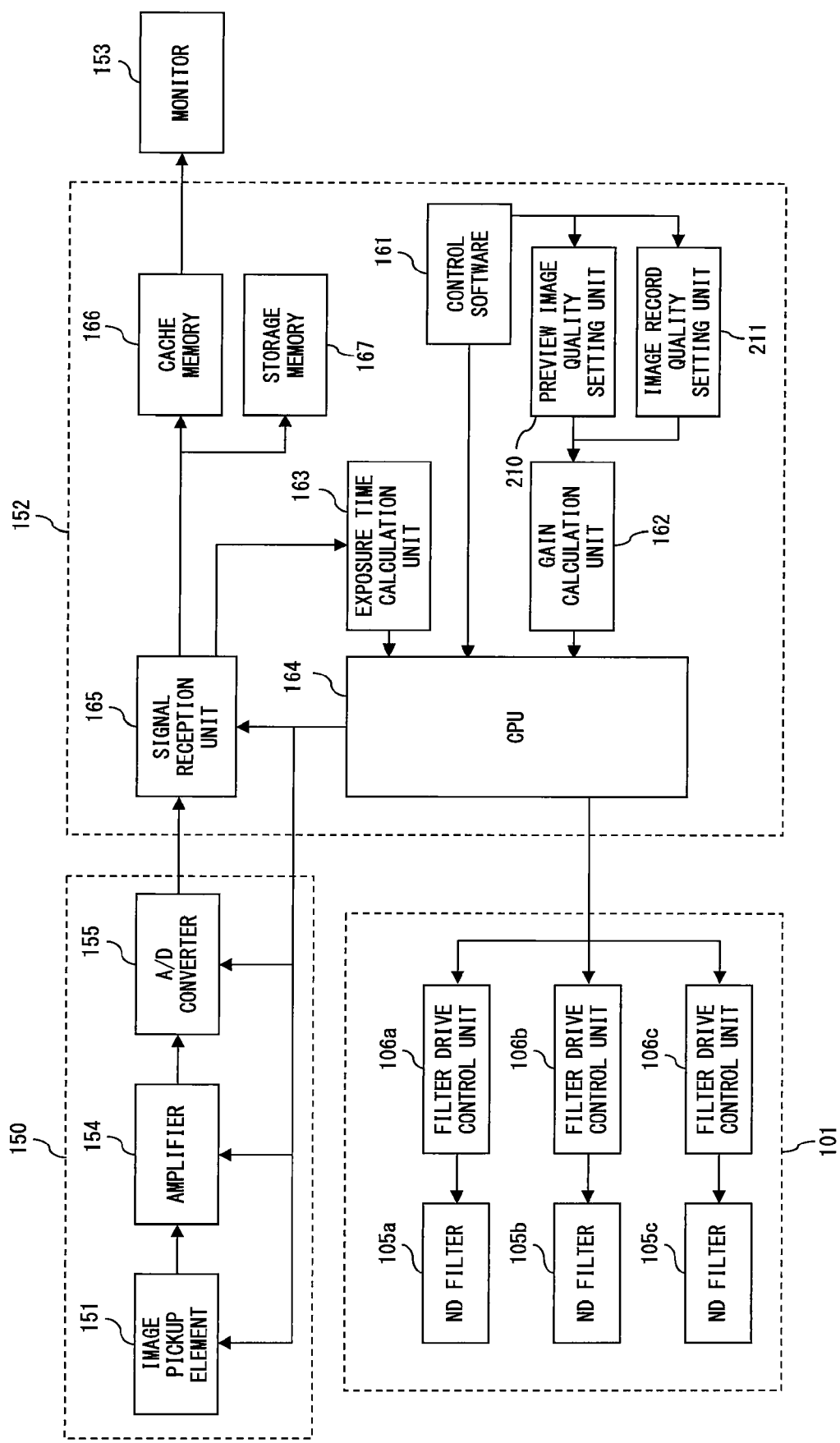
FIG. 7 shows the internal configuration of the microscope image pickup system according to the third embodiment.

FIG. 7 shows the internal configuration of the microscope image pickup system according to the third embodiment. FIG. 8A shows the operation condition of the preview image quality setting unit provided for the microscope image pickup system according to the third embodiment. FIG. 8B shows the operation condition of the image record quality setting unit provided for the microscope image pickup system according to the third embodiment. In FIG. 7, the same configuration as in the first or second embodiment is assigned the same reference numeral, and the description is omitted.

As shown in FIG. 7, the microscope image pickup system according to the third embodiment has the PC 152 further provided with a preview image quality setting unit 210 and an image record quality setting unit 211 in addition to the control software 161, the gain calculation unit 162, the exposure time calculation unit 163, the CPU 164, the signal reception unit 165, the cache memory 166, and the storage memory 167. The image quality level of the preview image quality setting unit 210 and the image record quality setting unit 211 is set according to the instruction transmitted from an observer through the control software 161.

The preview image quality setting unit 210 selects the ND filter 105 to be used in the preview mode from among the ND filters 105a through 105c depending on the image quality level or the fading suppression level set by an observer, and transmits a signal indicating the selected ND filter 105 to the gain calculation unit 162.

The image record quality setting unit 211 selects the ND filter 105 used in the image record mode from among the ND filters 105a through 105c depending on the image quality level of the fading suppression level set by an observer, and transmits a signal indicating the selected ND filter 105 to the gain calculation unit 162.

The respective operation conditions of the preview image quality setting unit 210 and the image record quality setting unit 211 are described below with reference to FIGS. 8A and 8B.

The preview image quality setting unit 210 and the image record quality setting unit 211 select the ND filter 105 to be used depending on the image quality level or the fading suppression level. Since the relationship among the transmittance Na of the ND filter 105a, the transmittance Nb of the ND filter 105b, and the transmittance Nc of the ND filter 105c is expressed by 1>Na>Nb>Nc, the collation of the gain values set for the gain value Gp and the gain value Ge is expressed by Gs<Gs/Na<Gs/Nb<Gs/Nc. Since the image quality level is inversely proportional to the gain value, it is the image quality level (low, medium, and high) as shown in FIGS. 8A and 8B depending on the gain values set. Similarly, since the fading suppression level is inversely proportional to the transmittance N of the ND filter 105 it is the fading suppression level (low, medium, and high) as shown in FIGS. 8A and 8B depending on the transmittance N of the ND filter 105 to be used.

The preview image quality setting unit 210 selects the ND filter 105 depending on the image quality level or the fading suppression level in the preview mode set by an observer. The gain calculation unit 162 calculates the gain value Gp depending on the transmittance N of the ND filter 105 to be used. For example, if the observer sets the image quality level in the preview mode as "low", or the fading suppression level as "high", the preview image quality setting unit 210 selects the ND filter 105c, and transmits a signal indicating the selected ND filter 105c to the gain calculation unit 162. The gain calculation unit 162 calculates the gain value Gp=Gs/Nc, and transmits the calculated gain value Gp to the CPU 164.

Similarly, the image record quality setting unit 211 selects the ND filter 105 depending on the image quality level or the fading suppression level in the image record mode set by an observer. The gain calculation unit 162 calculates the gain value Ge depending on the transmittance N of the ND filter 105 to be used. For example, when the observer sets the image quality level in the image record mode as "medium", or the fading suppression level as "medium", the image record quality setting unit 211 selects the ND filter 105a, and transmits a signal indicating the selected ND filter 105a to the gain calculation unit 162. The gain calculation unit 162 calculates the gain value Gp=Gs/Na, and transmits the calculated gain value Gp to the CPU 164.

Before entering the preview mode and the image record mode, the observer sets the image quality level or the fading suppression level in the preview mode, and the image quality level or the fading suppression level in the image record mode through the control software 161 in advance. The operations of the microscope image pickup system in the subsequent preview mode and the image record mode are the same as those in the first and the second embodiments.

In the microscope image pickup system according to the third embodiment, an observer can select a setting item in the preview mode or the image record mode such as "high image quality level or low fading suppression level", "low image quality level or high fading suppression level", "medium image quality level or medium fading suppression level", etc. Thus, the fading can be suppressed appropriately depending on the use or intention of the observer.

In addition, according to the microscope image pickup system of the third embodiment, the gain value Gp of the amplifier 154 is set high depending on the transmittance N of the ND filter 105 in the preview mode. Therefore, the intensity of the fluorescence 111 of the sample 110 is equivalent to the intensity of the fluorescence 111 of the sample 110 to be originally observed when the ND filter 105 is removed, thereby successfully maintaining the convenience during observation. Also in the image record mode, the gain value Gp of the amplifier 154 is set higher depending on the transmittance N of the ND filter 105. Therefore, the intensity of the fluorescence 111 of the sample 110 is equivalent to the intensity of the fluorescence 111 of the sample 110 to be originally observed when the ND filter 105 is removed, thereby storing clear observed images.

In the above-mentioned embodiments, a number of variations can be realized within the scope of the microscope image pickup system of the present invention.

Figure 9:
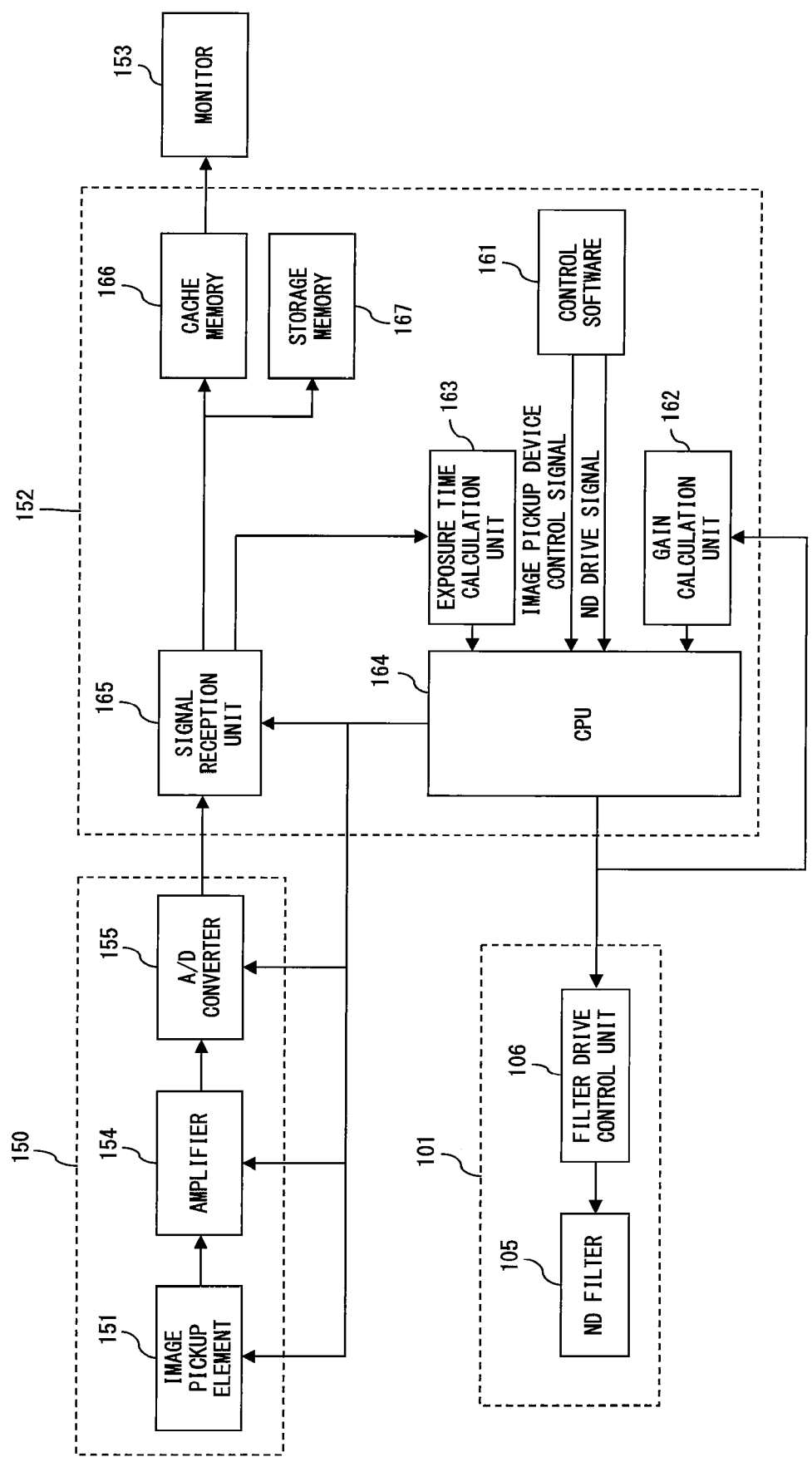
FIG. 9 shows the internal configuration of the microscope image pickup system according to another embodiment.

That is, in the above-mentioned embodiments, the gain value Gp or the gain value Ge of the amplifier 154 of the image pickup device 150 is calculated depending on the switch of the preview mode and the image record mode, but an observer can calculate the gain value Gp or the gain value Ge of the amplifier 154 depending on the insert/remove state of the ND filter 105 by manually inserting/removing the ND filter 105. For example, as the microscope image pickup system shown in FIG. 9, the microscope image pickup system is configured such that an image pickup device control signal and an ND drive signal are transmitted from the control software 161 to the CPU 164 independently of each other so that the image pickup device 150 and the ND filter 105 can be independently controlled. Then, a drive signal of the ND filter 105 is transmitted from the CPU 164 to the filter drive control unit 106, and simultaneously the drive signal is also transmitted to the gain calculation unit 162 to direct the gain calculation unit 162 to calculate the gain value Gp or the gain value Ge. With the configuration, as in the above-mentioned embodiments, a clear preview image can be acquired with the fading suppressed and the gain value Gp of the amplifier 154 raised by inserting the ND filter 105 in the preview mode, and a clear storage images can be acquired by removing the ND filter 105 and reducing the gain value Ge of the amplifier 154 in the image record mode.

In the above-mentioned embodiments, still images are recorded in the storage memory 167 in the image record mode, but moving pictures can be recorded in the storage memory 167 in the image record mode using the image pickup device 150 capable of capturing moving pictures.

In the above-mentioned embodiments, the sample 110 can be prevented from being faded by inserting/removing the ND filter 105, but the present invention is not limited to the application, and the fading of the sample 110 can be suppressed by adjusting the pulse width modulation (PWM) of the light source 103, adjusting the turn-on interval of a light emitting diode (LED) as the light source 103, adjusting the power supply voltage of the light source 103, etc.

In addition, according to the above-mentioned embodiments, a signal value indicating an image captured by the image pickup device 150 is amplified by raising the gain value of the amplifier 154, but a signal value indicating an image captured by the image pickup device 150 can be amplified by binning, that is, adding and outputting a plurality of signal values. Furthermore, the image pickup device 150 can increase signal values indicating images captured by the image pickup device 150 by extending the exposure time of the image pickup element 151.

Additionally, in the above-mentioned embodiments, white balance and black balance in the image pickup device 150 can be simultaneously adjusted depending on the intensity o the light source 103 during adjustment of light quantity.

What is claimed is:

1. A microscope image pickup system, comprising:
   a light source which emits illumination light to a test object;
   an object lens mounted opposite the test object;
   a display device;
   a record device;
   a capture device which selectively performs a preview mode in which an image of the test object obtained by the object lens is repeatedly captured and a plurality of captured images are continuously displayed on the display device, or an image record mode in which the image of the test object is captured and the captured image is recorded on the record device;
   an illumination light amount control device which controls an amount of the illumination light; and
   a system control device which controls an operation of the illumination light amount control device depending on which one of the preview mode and the image record mode is performed by the capture device.

2. The microscope image pickup system according to claim 1, wherein the system control device controls an operation of the capture device depending on which one of the preview mode and the image record mode is performed by the capture device.

3. The microscope image pickup system according to claim 1, wherein the system control device controls an operation of the capture device depending on the operation of the illumination light amount control device.

4. The microscope image pickup system according to claim 1, further comprising a calculation device which calculates an amount of the illumination light in the preview mode, wherein the system control device controls the operation of the illumination light amount control device and an operation of the capture device depending on the amount of light calculated by the calculation device.

5. The microscope image pickup system according to claim 1, further comprising an image quality adjustment device which adjusts image quality to one of a plurality of stages of image quality, wherein the system control device controls the operation of the illumination light amount adjustment device and an operation of the capture device depending on a combination of which one of the plurality of stages of image quality is set at the image quality adjustment device and which one of the preview mode and the image record mode is performed by the capture device.

6. A microscope image pickup system, comprising:
a light source which emits illumination light to a test object;
an object lens mounted opposite the test object;
a capture device which captures an image of the test object by the object lens;
an illumination light amount control device which controls an amount of the illumination light; and
a system control device which raises an amplification rate of a signal value indicating an image captured by the capture device when the amount of light of the illumination light becomes small due to an operation of the illumination light amount control device.

7. The microscope image pickup system according to claim 1, wherein the operation of the illumination light amount control device comprises controlling the amount of illumination light by inserting or removing a darkening filter between the test object and the light source or adjusting intensity of the illumination light of the light source.

8. The microscope image pickup system according to claim 2, wherein the operation of the illumination light amount control device comprises controlling the amount of illumination light by inserting or removing a darkening filter between the test object and the light source or adjusting intensity of the illumination light of the light source.

9. The microscope image pickup system according to claim 3, wherein the operation of the illumination light amount control device comprises controlling the amount of illumination light by inserting or removing a darkening filter between the test object and the light source or adjusting intensity of the illumination light of the light source.

10. The microscope image pickup system according to claim 4, wherein the operation of the illumination light amount control device comprises controlling the amount of illumination light by inserting or removing a darkening filter between the test object and the light source or adjusting intensity of the illumination light of the light source.

11. The microscope image pickup system according to claim 5, wherein the operation of the illumination light amount control device comprises controlling the amount of illumination light by inserting or removing a darkening filter between the test object and the light source or adjusting intensity of the illumination light of the light source.

12. The microscope image pickup system according to claim 6, wherein the operation of the illumination light amount control device comprises controlling the amount of illumination light by inserting or removing a darkening filter between the test object and the light source or adjusting intensity of the illumination light of the light source.

13. The microscope image pickup system according to claim 2, wherein the operation of the capture device comprises adjusting an amplification rate of a signal value indicating the image, adjusting exposure time, adjusting white balance, or adjusting black balance.

14. The microscope image pickup system according to claim 3, wherein the operation of the capture device comprises adjusting an amplification rate of a signal value indicating the image, adjusting exposure time, adjusting white balance, or adjusting black balance.

15. The microscope image pickup system according to claim 4, wherein the operation of the capture device comprises adjusting an amplification rate of a signal value indicating the image, adjusting exposure time, adjusting white balance, or adjusting black balance.

16. The microscope image pickup system according to claim 5, wherein the operation of the capture device comprises adjusting an amplification rate of a signal value indicating the image, adjusting exposure time, adjusting white balance, or adjusting black balance.

17. The microscope image pickup system according to claim 6, wherein the system control device adjusts at least one of exposure time, white balance, and black balance of the capture device.

18. The microscope image pickup system according to claim 4, wherein the operation of the illumination light amount control device comprises controlling the amount of illumination light by inserting or removing a darkening filter between the test object and the light source, wherein the inserted darkening filter is selected from among a plurality of darkening filters based on the amount of light calculated by the calculation device.

19. The microscope image pickup system according to claim 5, wherein the operation of the illumination light amount control device comprises controlling the amount of illumination light by inserting or removing a darkening filter between the test object and the light source, wherein the inserted darkening filter is selected from among a plurality of darkening filters based on said combination of which one of the plurality of stages of image quality is set at the image quality adjustment device and which one of the preview mode and the image record mode is performed by the capture device.

* * * * *